(12) United States Patent
Yoon et al.

(10) Patent No.: US 10,441,526 B2
(45) Date of Patent: Oct. 15, 2019

(54) LIQUID OIL DISPERSION COSMETIC COMPOSITION

(71) Applicant: AMOREPACIFIC CORPORATION, Seoul (KR)

(72) Inventors: Se Rim Yoon, Yongin-si (KR); Kyung Nam Kim, Yongin-si (KR); Kyung Ho Choi, Yongin-si (KR); Yeong Jin Choi, Yongin-si (KR)

(73) Assignee: AMOREPACIFIC CORPORATION, Yongsan-Gu, Seoul (KR)

( * ) Notice: Subject to any disclaimer, the term of this patent is extended or adjusted under 35 U.S.C. 154(b) by 0 days.

(21) Appl. No.: 15/740,156

(22) PCT Filed: Jun. 21, 2016

(86) PCT No.: PCT/KR2016/006558
§ 371 (c)(1),
(2) Date: Dec. 27, 2017

(87) PCT Pub. No.: WO2017/003122
PCT Pub. Date: Jan. 5, 2017

(65) Prior Publication Data
US 2018/0185267 A1 Jul. 5, 2018

(30) Foreign Application Priority Data
Jun. 30, 2015 (KR) .................. 10-2015-0093770

(51) Int. Cl.
| | | |
|---|---|---|
| *A61K 8/891* | (2006.01) | |
| *A61Q 17/04* | (2006.01) | |
| *A61Q 19/00* | (2006.01) | |
| *A61K 8/04* | (2006.01) | |
| *A61K 8/19* | (2006.01) | |
| *A61K 8/25* | (2006.01) | |
| *A61K 8/27* | (2006.01) | |
| *A61K 8/29* | (2006.01) | |
| *A61K 8/31* | (2006.01) | |
| *A61K 8/58* | (2006.01) | |
| *A61K 8/893* | (2006.01) | |
| *A61K 8/894* | (2006.01) | |

(52) U.S. Cl.
CPC ............... *A61K 8/891* (2013.01); *A61K 8/04* (2013.01); *A61K 8/19* (2013.01); *A61K 8/25* (2013.01); *A61K 8/27* (2013.01); *A61K 8/29* (2013.01); *A61K 8/31* (2013.01); *A61K 8/585* (2013.01); *A61K 8/893* (2013.01); *A61K 8/894* (2013.01); *A61Q 17/04* (2013.01); *A61Q 19/00* (2013.01); *A61K 2800/5422* (2013.01)

(58) Field of Classification Search
CPC ..................................................... A61Q 19/00
See application file for complete search history.

(56) References Cited

U.S. PATENT DOCUMENTS

| | | | |
|---|---|---|---|
| 9,492,370 B2 * | 11/2016 | Choi | ............ A61K 8/0204 |
| 10,092,498 B2 * | 10/2018 | Choi | .................. A61K 8/06 |
| 2014/0341959 A1 * | 11/2014 | Choi | ............ A61K 8/0204 |
| | | | 424/401 |
| 2015/0104235 A1 | 4/2015 | Choi et al. | |
| 2018/0360730 A1 * | 12/2018 | Choi | ............ A61K 8/0204 |

FOREIGN PATENT DOCUMENTS

| | | | |
|---|---|---|---|
| CN | 102246014 A | 11/2011 | |
| KR | 19970032792 A | 7/1997 | |
| KR | 100797072 B1 | 1/2008 | |
| KR | 101210371 B1 | 12/2012 | |
| KR | 20130083852 A * | 7/2013 | ....... A61K 8/0204 |
| KR | 1020130116044 A | 10/2013 | |
| KR | 1020140060927 A | 5/2014 | |
| WO | 2010068687 A1 | 6/2010 | |

OTHER PUBLICATIONS

Delvalle et al. "New formulation possibilities with a water-in-oil silicone emulsifier suitable for PEG-free systems", Dow Corning, 2014. (Year: 2014).*
International Search report for PCT/KR2016/006558, dated Sep. 21, 2016 (4 pages with translation).

* cited by examiner

*Primary Examiner* — Gina C Justice
(74) *Attorney, Agent, or Firm* — Cantor Colburn LLP

(57) ABSTRACT

A liquid oil dispersion cosmetic composition of the present invention is capable of implementing a refreshing and light feeling and has excellent dispersibility by containing surfactants, powders, and volatile substances having fast volatility, low viscosity and low density. In addition, the liquid oil dispersion cosmetic composition, according to the present invention, can prevent precipitation of the powders by being uniformly impregnated in between the pores of foam carriers, and thus, can maintain high formulation stability even during long-term storage.

13 Claims, 3 Drawing Sheets

[Fig 1]
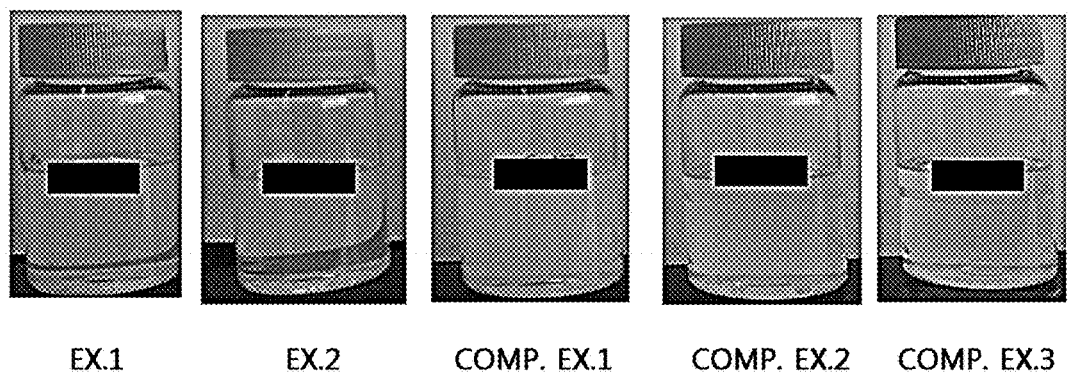
EX.1    EX.2    COMP. EX.1    COMP. EX.2    COMP. EX.3
[Fig 2]
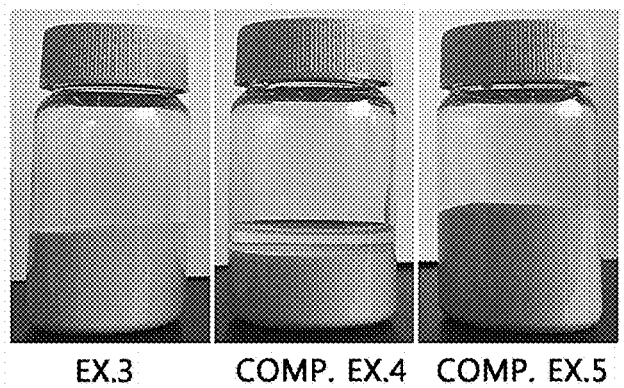
EX.3    COMP. EX.4    COMP. EX.5

[Fig 3]
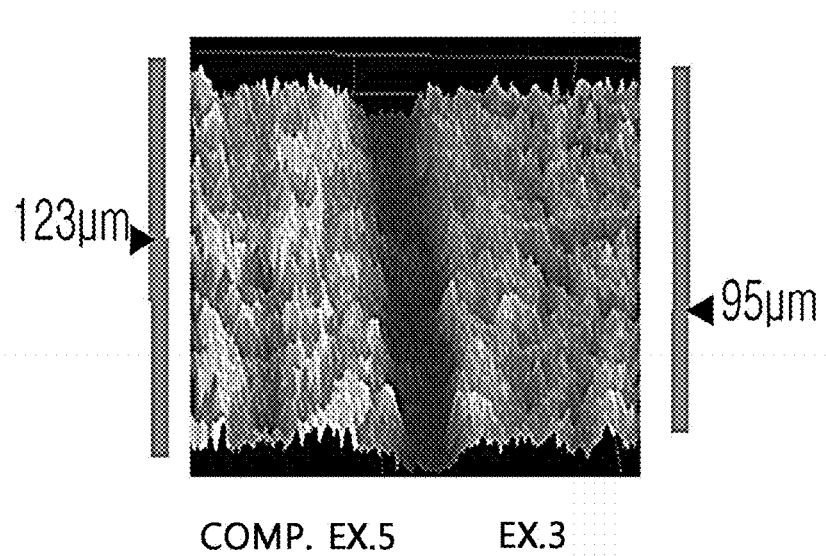
COMP. EX.5    EX.3
[Fig 4]
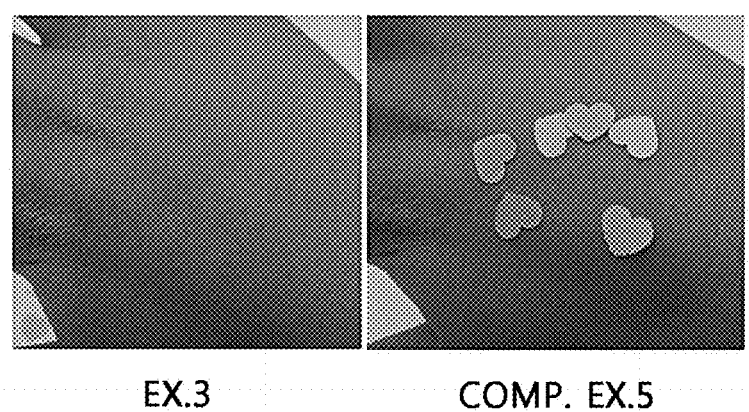
EX.3    COMP. EX.5

[Fig 5]
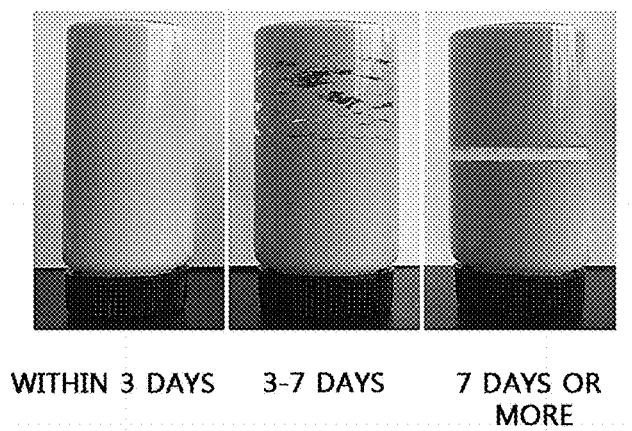
WITHIN 3 DAYS　　3-7 DAYS　　7 DAYS OR MORE
[Fig 6]
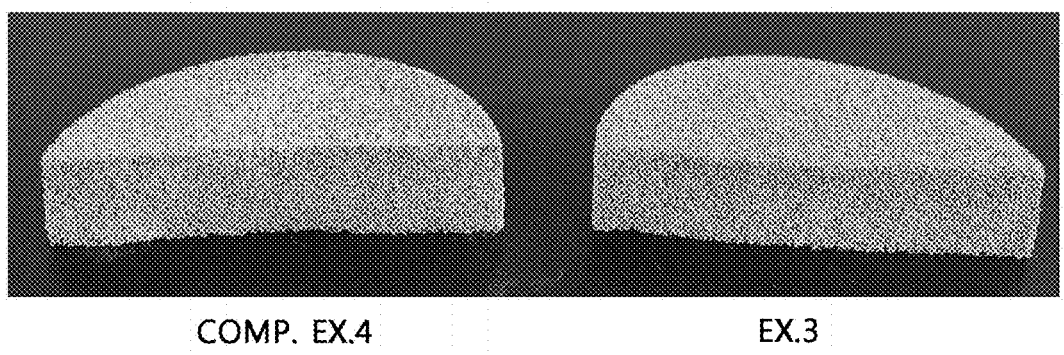
COMP. EX.4　　　　　　EX.3

LIQUID OIL DISPERSION COSMETIC COMPOSITION

This application is a national stage application of PCT/KR2016/006558, filed Jun. 21, 2016, which claims priority to KR 10-2015-0093770, filed Jun. 30, 2015, both of which are hereby incorporated by reference in their entirety.

TECHNICAL FIELD

The present disclosure relates to an oil-dispersed liquid type cosmetic composition having improved stability.

BACKGROUND ART

In general, makeup cosmetic compositions are classified into water-in-oil type compositions and oil-in-water type compositions. Oil-in-water type compositions have excellent makeup persistency but are heavy and tacky, while water-in-oil type compositions have an advantage of a high moisturizing feel but show low persistency.

As cosmetic compositions that supplement such disadvantages of oil-in-water type and water-in-oil type compositions, oil-dispersed liquid type cosmetic compositions merely including powder and oil have been developed. However, since the conventional oil-dispersed liquid type cosmetic composition is a liquid formulation including powder simply dispersed in oil, it causes oil-powder separation with ease due to the gravity, and thus requires sufficient shaking and dispersion on every use thereof inconveniently. In addition, oil and powder may be mixed and dispersed non-homogeneously, and thus a caking phenomenon of precipitation and entanglement of powder may occur with ease.

Particularly, in the case of an oil-dispersed liquid type cosmetic composition for use in protecting UV rays, the oil with low polarity and the organic/inorganic UV protecting agents with high polarity may not be present in a dispersed state but may be separated from each other unstably, resulting in a limitation in realizing a high sun protection factor.

REFERENCES

Patent Document

Korean Laid-Open Patent No. 1997-0032792

DISCLOSURE

Technical Problem

A technical problem to be solved by the present disclosure is to provide an oil-dispersed liquid type cosmetic composition having improved formulation stability.

Another technical problem to be solved by the present disclosure is to provide an oil-dispersed liquid type cosmetic composition having improved convenience of use.

Still another technical problem to be solved by the present disclosure is to provide an oil-dispersed liquid type cosmetic composition having an excellent sun protection factor.

Technical Solution

In one general aspect, there is provided an oil-dispersed liquid type cosmetic composition including a volatile material having a density of 0.6-0.9 g/mL, a non-ionic silicone surfactant having a density of 0.9-1.1 g/mL and an HLB (hydrophile-lipophile balance) of 1-6, and powder.

In another general aspect, there is provided a cosmetic product including the oil-dispersed liquid type cosmetic composition and a foam carrier in which the oil-dispersed liquid type cosmetic composition is impregnated.

In still another general aspect, there is provided an oil-dispersed liquid type composition which has a sun protection factor (SPF) of 30 or more and a protection grade of UVA (PA) of PA++ to PA+++, and a cosmetic product including the same.

Advantageous Effects

According to the embodiments of the present disclosure, it is possible to realize a fresh and light feel of use by using a volatile material having a high evaporation rate and low viscosity, to minimize the interfacial tension between oil phases through a surfactant and to improve the dispersibility of powder having high polarity. After the application to the skin, the volatile material evaporates and only the powder remains, and thus it is possible to realize persistency at least equal to the persistency of an oil-in-water type makeup cosmetic agent.

In addition, the oil-dispersed liquid type cosmetic composition according to the present disclosure is impregnated uniformly in the pores of a foam carrier to prevent precipitation of powder and retains a formulation in which a volatile material and powder are dispersed uniformly, even when it is stored for a long time. As a result, the oil-dispersed liquid type cosmetic composition does not cause inconvenience of shaking the cosmetic product before use, and thus provides high convenience of use.

When applying a UV protecting agent to the oil-dispersed liquid type cosmetic composition according to the present disclosure, it is possible to realize excellent formulation stability and a high sun protection factor.

DESCRIPTION OF DRAWINGS

FIG. 1 is a photographic view illustrating the results of degrees of oil phase separation in Examples 1 and 2 (oil-dispersed liquid type compositions) and Comparative Examples 1-3, as observed by the naked eyes 7 days after the preparation thereof.

FIG. 2 is a photographic view illustrating the results of degrees of oil phase separation in the upper and lower layers and powder dispersibility in Example 3 (oil-dispersed liquid type composition) and Comparative Examples 4 and 5, as observed by the naked eyes.

FIG. 3 is a photographic view illustrating the results of determining thickness upon skin application of the oil-in-water type cosmetic composition in Comparative Example 5 (left side) impregnated in a foam carrier and the oil-dispersed liquid type cosmetic composition in Example 3 (right side) impregnated in a foam carrier.

FIG. 4 is a photographic view illustrating the results of determining stickiness of Example 3 impregnated in a foam carrier and Comparative Example 5 impregnated in a foam carrier.

FIG. 5 is a photographic view illustrating the results of observing whether the formulation of Example 3 is separated or not as a function of storage time.

FIG. 6 is a photographic view illustrating the appearance of each of Example 3 and Comparative Example 4 supported on urethane foam as taken 3 months after they are supported.

BEST MODE

Exemplary embodiments now will be described more fully hereinafter.

In one aspect, there is provided an oil-dispersed liquid type cosmetic composition including a volatile material having low density, a surfactant and powder.

According to an embodiment, the volatile material may have a density of 0.6-0.9 g/mL, more particularly 0.7-0.85 g/mL at 25° C. room temperature.

The volatile material may include any volatile material, as long as it improves the dispersibility of powder in the composition to improve formulation stability and provides high spreadability and a fresh feel of use. Herein, 'volatile material' means a material 20% of which evaporates when it is allowed to stand at room temperature for 2 hours. For example, the volatile material may include at least one material selected from the group consisting of: at least one volatile silicone oil selected from cyclomethicone, trimethicone and dimethicone having a viscosity of 2.0 centistock (cs) or lower; at least one volatile hydrocarbon oil selected from isododecane and dodecane; and ethanol. The volatile material may be used alone or in combination, if necessary. The viscosity of dimethicone is determined according to Viscosity Measurement 1 in the general test methods of the Korean Pharmacopoeia and is measured by using an Ubbelohde type viscometer, introducing the viscometer to the specified thermostat at 25° C. so that it may be immersed completely therein, allowing the viscometer to stand vertically, and allowing the sample to stand for 20 minutes so that it may reach the same temperature.

In the case of oil-dispersed liquid type cosmetic compositions, those using non-volatile hydrocarbon oil having a high oily feel or heavy ester oil may show a heavy and sticky feel of use. However, such volatile silicone oil, volatile hydrocarbon oil and ethanol evaporate rapidly when applying the cosmetic composition to the skin, and thus show a light feel of use and provide excellent advantages during use, such as spreadability and applicability. In addition, they provide safety, high waterproof property and a moisturizing/screening effect.

According to another embodiment, the oil-dispersed liquid type cosmetic composition may include the volatile material in an amount of 0.1-80 wt %, more particularly 10-70 wt %, based on the total weight of the composition. When the amount is larger than 70 wt %, skin pruritus and irritation may occur undesirably. When the amount is less than 10 wt %, only a sticky and heavy feel of oil residue remains so that a fresh feel of use may not be obtained.

Since the volatile material has low polarity and is significantly lighter than silicone oil, ester oil or hydrocarbon oil having a density of 1.0-1.3 g/mL, it floats easily on the upper layer portion upon the mixing with highly polar powder due to the gravity and is separated easily after several hours, resulting in low compatibility. For example, in the case of a UV protecting composition, most organic UV protecting agents are highly polar organic oil and inorganic UV protecting agents are also inorganic powder having high surface polarity and high density. Thus, when such UV protecting agents are mixed with the oil having low specific gravity, the oil phase of the upper layer portion may be separated with ease and the inorganic UV protecting agents may be precipitated in the lower layer portion. As a result, it is difficult to ensure a uniform sun protection factor in the whole formulation of the composition. For this, some product series requiring shaking upon every use have been commercialized but they are inconvenient to use and are not favorable to ensuring a high sun protection factor.

Under these circumstances, the oil-dispersed liquid type cosmetic composition may include, as a surfactant for stabilizing two systems having different densities (a highly polar ester oil phase (except UV protecting agents) and a non-polar silicone oil phase) in its oil phase, and for ensuring the formulation stability of the composition, a non-ionic silicone surfactant having a density of 0.9-1.1 g/mL, more particularly 0.95-1.0 g/mL, and an HLB (hydrophile-lipophile balance) of 1-6. Such a surfactant reduces a difference in density between the oil phase ingredients in the composition and minimizes the interfacial tension, and thus can inhibit separation in the oil phase.

According to an embodiment, the surfactant may include a silicone surfactant containing at least one of polyethylene glycol (PEG), polypropylene glycol (PPG) and polyglyceryl groups. When the surfactant is a polymeric silicone surfactant having at least one of polyethylene glycol (PEG), polypropylene glycol (PPG) and polyglyceryl groups attached to the side chains in a comb-like shape, it is possible to improve the stability between oil phases and to improve the dispersibility of highly polar powder. For example, the surfactant that may be used is at least one selected from the group consisting of silicones such as PEG-10 dimethicone, cetyl PEG/PPG-10/1 dimethicone, lauryl PEG-9 polydimethylsiloxyethyl dimethicone, cyclopentasiloxane/PEG-.PPG-19.19 dimethicone and lauryl PEG.PPG-18.18 methicone, but is not limited thereto.

According to still another embodiment, the surfactant may be used in an amount of 0.01-10 wt %, more particularly 0.1-5 wt %, based on the total weight of the composition. When the amount is less than 0.1 wt %, the powder shows low dispersibility. When the amount is larger than 5 wt %, a sticky feel is generated to hinder a fresh feel of use and to cause a unique off-flavor severely.

The composition according to an embodiment of the present disclosure may be used for UV protection and may include a UV protecting agent in this case. For example, such a UV protecting composition may have a sun protection factor (SPF) of 30 or more and a protection grade of UVA (PA) of PA++ to PA+++. An organic UV protecting agent or inorganic UV protecting agent may be used alone or in combination as UV protecting agent. Particularly, the organic UV protecting agent that may be used includes octylmethoxy cinnamate, octylsalicylate, octocrylene, butylmethoxydibenzoylmethane, oxybenzone, octyltrizaone, menthylanthranilate, 3,4-methylbenzylidene camphor, isoamyl-p-methoxycinnamate, bisethylhexyloxyphenol methoxyphenyltriazine, methylene bisbenzotriazolyltetramethylbutylphenol, or the like. The inorganic UV protecting agent that may be used includes powder such as titanium dioxide having an average particle size of 5-100 nm, zinc oxide having an average particle size of 5-300 nm, iron oxide having an average particle size of 5-300 nm, or the like. Herein, as the average particle size of the inorganic UV protecting agent increases, a whitening phenomenon becomes severe upon the skin application, resulting in degradation of product value. On the contrary, an excessively small particle size may cause infiltration into the skin and skin irritation. Thus, considering a whitening phenomenon, the average size is 300 nm or less preferably. In addition, considering skin irritation and skin whitening at the same time, the average size is 10-50 nm preferably.

Further, the UV protecting agent may be used in an amount of 1-35 wt % based on the total weight of the composition. When the UV protecting agent is used in an amount less than 1 wt %, the UV protecting effect is not sufficient (SPF of 10 or lower). When the UV protecting agent is used in an amount larger than 35 wt %, whitening or glittering becomes severe or skin irritation may occur.

The composition according to the present disclosure may include powder. The powder may be at least one selected from polymethyl methacarylate (PMMA), silica, nylon, polyurethane, ultramarine, iron oxide, pearl, synthetic mica, mica, talc, sericite and boron nitride, in addition to the inorganic UV protecting agent. The powder may be used in an amount of 0.1-50 wt % based on the total weight of the composition. When the powder (pigment) is used in an amount less than 0.1 wt %, it is not possible to provide a close contact feel and colorizing and thickening effects sufficiently. When the pigment is used in an amount larger than 50 wt %, the viscosity is increased excessively to provide a stiff feel of use and to cause agglomeration in the formulation.

The oil-dispersed liquid type cosmetic composition according to the present disclosure may be a low-viscosity composition and may have a viscosity of 2,000-15,000 centipoise (cps) in order to provide a fresh feel of use. In the present disclosure, the viscosity may be determined by using a viscometer, such as LVDV II+PRO, with spindle No. 63 at a spindle speed of 5 rpm. The above-defined viscosity range is significantly lower than the viscosity range (4,000-80,000 cps) of the conventional cosmetic composition impregnated in a carrier such as foam. Since the composition according to the present disclosure includes such a low-density volatile material, surfactant and powder, it optimizes a difference in specific gravity between oil phases and reduces a difference in polarity through stabilization of the interfacial film. As a result, even though the composition has such a low viscosity, it may be impregnated in a foam carrier uniformly without separation of the formulation.

For example, the oil-dispersed liquid type cosmetic composition may be formulated into sunscreen, makeup base, liquid foundation, BB cream, CC cream, concealer, makeup primer, lip gloss, or the like, but is not limited thereto.

In addition, the composition according to the present disclosure may further include supplementary ingredients, such as a pigment, fragrance, preservative and thickener, used generally when preparing a cosmetic composition.

In another aspect, there is provided a cosmetic product including the oil-dispersed liquid type cosmetic composition and a foam carrier in which the oil-dispersed liquid type cosmetic composition is impregnated. The cosmetic product according to the present disclosure provides the oil-dispersed liquid type cosmetic composition impregnated in a foam carrier, and thus provides a cosmetic product capable of retaining high formulation stability even when it is stored for a long time.

As used herein, the term 'carrier' means one capable of supporting any material, such as a composition, or any ingredient, and is used interchangeably with 'carrier body', 'impregnation material' or 'medium'. In addition, 'carrier' may be one used in such a manner that the material supported thereby may be discharged to a separate applicator. The composition supported in the carrier may be transferred to the skin, for example, through an application means (also referred to as an application instrument or applicator), such as a hand, puff, tip or brush.

In addition, as used herein, the term 'foam carrier' means a material capable of supporting any material or any ingredient, such as a composition, includes rubber, fibers or resin formed like a sea sponge, and covers one capable of supporting and discharging a cosmetic composition. Particularly, the foam may be natural foam or synthetic foam, but is not limited thereto. For example, the natural foam may include a sea sponge, natural rubber, or the like. The synthetic foam may include a synthetic resin, polyurethane, latex, acrylonitrile-butadiene rubber (NBR), butadiene rubber (BR), styrene-butadiene rubber (SBR), natural rubber (NR), chloroprene rubber (CR), butyl rubber (isoprene-isobutylene rubber: IIR), isoprene rubber (IR), vulcanized ethylene-propylene rubber (EPR), polysulfide rubber, silicone rubber, fluororubber, urethane rubber, acrylic rubber, ethylene propylene diene monomer (EPDM) rubber, polyvinyl alcohol (PVA), ethylene vinyl acetate (EVA), nitrile rubber (NR), or the like.

As used herein, the polyurethane foam as a kind of foam may include polyether-based foamed urethane (containing ether polyol as a main base), polyester-based foamed urethane or polycarbonate-based foamed urethane, but is not limited thereto. Particularly, the polyurethane foam may include polyether-based foamed urethane.

In addition, the polyether-based foamed urethane includes polyether-based dry foamed urethane and polyether-based wet foamed urethane. The polyester-based foamed urethane includes polyester-based dry foamed urethane and polyester-based wet foamed urethane. The polycarbonate-based foamed urethane includes polycarbonate-based dry foamed urethane and polycarbonate-based wet foamed urethane.

According to an embodiment, the foamed carrier may include pores so that the oil-dispersed liquid type cosmetic composition according to the present disclosure may be impregnated in the pores of the foam and may be maintained in a state distributed uniformly in the carrier.

According to another embodiment, the foam carrier may include pores having an average size of 30-2500 μm. The pore size is the average value of measurements determined by using an optical microscope (NIKON ELIPSE 80i). When the average pore size of the foam carrier is less than 30 μm, the pore space for supporting the cosmetic composition is too small to provide good supportability. When the average pore size is larger than 2500 μm, the pore space is too large to provide good controllability in discharging the composition. As used herein, the term 'supportability' means the ability of receiving and retaining any material or ingredient. The supportability required for a carrier is differentiated from taking a material temporarily on an applicator in that a composition is supported homogeneously for a long time. In addition, the term 'dischargeability' or 'discharge capability' means an amount of cosmetic composition discharged when the cosmetic composition is taken out of the carrier supporting the same by using an applicator. It is preferred that an adequate amount of cosmetic composition is discharged, no more and no less than that.

According to still another embodiment, the foam carrier may include 55-130 pores per inch (ppi). When the foam carrier has a pore number per inch larger than 130 ppi, the pore size is too small to control the flowability of the cosmetic composition and the absorption or discharge of the cosmetic composition. When the foam carrier has a pore number per inch less than 55 ppi, the foam carrier may show poor supportability after a cosmetic composition is supported. As used herein, the term 'pore number' refers to a pore number per inch of urethane foam. Herein, the pore number may be an average number of pores present on 1 inch line of width and length, measured precisely by W1-QA-14 (ASTM standard).

According to still another embodiment, the foam may have a density of 0.05-0.2 $g/cm^3$, particularly 0.1-0.18 $g/cm^3$. When the foam has a density less than 0.05 $g/cm^3$, the cosmetic composition is discharged in an excessively large amount, resulting in inconvenience of use. When the foam has a density larger than 0.2 g/cm$^3$, the cosmetic composition cannot be packed and discharged well.

As used herein, the term 'durability' means how much the foam retains its state without melting, tearing or swelling, when a cosmetic composition is supported by the foam and allowed to stand at a predetermined temperature for a predetermined time and/or how much the foam resists repeated pressure applied by an applicator when a cosmetic composition is taken out of the foam with the applicator during use.

According to still another embodiment, the foam may have a thickness of 1 mm-50 mm. When the foam has a thickness less than 1 mm, the amount of cosmetic composition supported by the foam is low. When the foam has a thickness larger than 50 mm, it is difficult to discharge the cosmetic composition during use without any residual amount of contents. The carrier using the foam according to an embodiment may have a thickness of 3 mm-45 mm, for example, 5 mm-40 mm, such as 8 mm-35 mm, particularly 10 mm-30 mm. More particularly, the thickness may be 50 mm or less, 40 mm or less, 30 mm or less, 20 mm or less, 10 mm or less, or 5 mm or less, and 1 mm or more, 10 mm or more, 20 mm or more, 30 mm or more, 40 mm or more, or 50 mm or more.

In the cosmetic product according to an embodiment of the present disclosure, the oil-dispersed liquid type cosmetic composition is impregnated in the foam carrier, and thus the oil-dispersed liquid type cosmetic composition may be confined uniformly in the pores of the carrier. Therefore, it is possible to prevent precipitation of powder, separation of a formulation and caking, when the oil-dispersed liquid type cosmetic composition is stored for a long time of several months or more. As a result, it is possible to provide a cosmetic product having improved formulation stability and convenience of use.

In addition, the cosmetic product according to some embodiments of the present disclosure may further include an applicator to take the oil-dispersed to liquid type cosmetic composition supported by the foam carrier. Further, the cosmetic product may be provided in the form of a cosmetic container called generally 'pact', which includes a lower part capable of receiving a carrier for a cosmetic composition and an upper lid part to which a mirror may be attached, but is not limited thereto.

MODES FOR INVENTION

Exemplary embodiments now will be described more fully hereinafter. The present disclosure may, however, be embodied in many different forms and should not be construed as limited to the exemplary embodiments set forth therein.

[Test Example 1] Comparison of Formulation Stability

To determine the oil separation rate at room temperature as formulation stability of the oil-dispersed liquid type cosmetic composition according to an embodiment of the present disclosure, only the oil phase ingredients except powder are mixed homogeneously as shown in the following Table 1 to provide compositions, and then the compositions are observed for their separation behaviors. Examples 1 and 2 are oil-dispersed formulations using a comb-like silicone surfactant containing PEG and PEG/PPG attached to the PDMS backbone as side chains as a non-ionic silicone emulsifier having an HLB of 1-6, Comparative Example 1 is an oil-dispersed formulation using a linear silicone surfactant, Comparative Example 2 is an oil-dispersed formulation using a sorbitan surfactant, and Comparative Example 3 is an oil-dispersed formulation using no surfactant. Each of the surfactants according to Examples 1 and 2 and Comparative Examples 1-3 has a density of 0.9-1.1 g/mL.

TABLE 1

| Ingredients (wt %) | Compound | Ex. 1 | Ex. 2 | Comp. Ex. 1 | Comp. Ex. 2 | Comp. Ex. 3 |
|---|---|---|---|---|---|---|
| Oil phase ingredients | Cyclopentasiloxane | Balance | Balance | Balance | Balance | Balance |
| | Trisiloxane | 20.00 | 20.00 | 20.00 | 20.00 | 20.00 |
| | Ethylhexylmethoxy cinnamate | 7.00 | 7.00 | 7.00 | 7.00 | 7.00 |
| | PEG-10 dimethicone | 2.00 | — | — | — | — |
| | Cetyl PEG.PPG-10.1 dimethicone | — | 2.00 | — | — | — |
| | polysilicone-13 | — | — | 2.00 | — | — |
| | Sorbitan sesquioleate | — | — | — | 2.00 | — |

Each of the compositions of Examples 1 and 2 and Comparative Examples 1-3 according to Table 1 is allowed to stand at room temperature for 7 days after the preparation thereof and degrees of oil separation are observed by the naked eyes. Observation is carried out right after the preparation, and 1 day and 7 days after the preparation. FIG. 1 is a photograph illustrating each of the compositions after 7 days. The results of evaluation of stability based on the above observation results are shown in the following Table 2.

TABLE 2

| Tested material | Right after preparation | 1 day | 7 days |
|---|---|---|---|
| Ex. 1 | ○ | ○ | ○ |
| Ex. 2 | ○ | ○ | ○ |
| Comp. Ex. 1 | ○ | △ | △ |
| Comp. Ex. 2 | ○ | △ | X |
| Comp. Ex. 3 | ○ | X | X |

<Stability evaluation criteria>
X: very poor (oil floating appears and separation occurs immediately)
△: slightly poor (oil floating does not appear but the formulation is opaque)
○: good (oil floating does not appear and the formulation is transparent)

As can be seen from Table. 2 and FIG. 1, Examples 1 and 2 cause no oil separation, while Comparative Examples 1 and 2 cause oil separation after 1 day and Comparative Example 3 causes separation of all oil phase ingredients and they provide unstable formulations. It is thought that the above results are the effect of increasing compatibility between different types of oil, because Examples 1 and 2 and Comparative Examples 1 and 2 using a surfactant minimize the interfacial tension between oil phases, as compared to Comparative Example 3 using no surfactant. Examples 1 and 2 show that the surfactants of polymers containing comb-like side chains have higher interfacial adsorption ability as compared to the linear polymer surfactants of Comparative Examples 1 and 2, resulting in improvement of interfacial stabilization.

[Test Example 2] Comparison of Sun Protection Factor Stability

To determine the sun protection factor stability of the oil-dispersed cosmetic composition according to an embodiment as a UV protecting composition, the following test is carried out.

First, an inorganic UV protecting agent is added as powder to an oil-dispersed formulation containing PEG-10 dimethicone as a surfactant to provide Example 3 and Comparative Example 4 as shown in the following Table 3. In addition, as another comparative example, an oil-in-water type composition of Comparative Example 5 is provided.

TABLE 3

| Ingredients (wt %) | Compound | Ex. 3 | Comp. Ex. 4 | Comp. Ex. 5 |
|---|---|---|---|---|
| Oil phase ingredients | Cyclopentasiloxane | Balance | Balance | Balance |
| | Trisiloxane | 20.00 | 20.00 | — |
| | Ethylhexylmethoxy cinnamate | 7.00 | 7.00 | 7.00 |
| | PEG-10 dimethicone | 2.00 | — | 2.00 |
| Powder | Titanium dioxide | 5.00 | 5.00 | 5.00 |
| | Zinc oxide | 10.00 | 10.00 | 10.00 |
| | Silica | 10.00 | 10.00 | 10.00 |
| | Iron oxide | 2.00 | 2.00 | 2.00 |
| Aqueous phase ingredients | Purified water | — | — | 40.00 |

Each of the compositions is allowed to stand at room temperature for 3 days, and then the dispersibility of the UV protecting agent is evaluated in the upper layer portion and the lower layer portion of each composition. The sun protection factors for the upper layer portion and the lower layer portion of each composition are measured and compared with each other to evaluate the stability.

The sun protection factor is measured based on the in vitro test method (No. 2001-44 noticed by Ministry of Food and Drug Safety) for the quality control of a UV protecting cosmetic composition. Particularly, 2 mg/cm$^2$ of a sample is applied uniformly to the surface of a test tape (Transpore™, 3M) and dried for 15 minutes, and then the sun protection factor of the sample is measured by using a sun protection factor measuring system (SPF 290 Analyzer, The Optometric Group, USA). The sun protection factor (hereinafter, "SPF") is determined as the average value of 3 measurements and the results are shown in Table 4 and FIG. 2.

TABLE 4

| Tested material | SPF of upper layer portion | SPF of lower layer portion |
|---|---|---|
| Ex. 3 | 53.4 | 54.1 |
| Comp. Ex. 4 | 34.2 | 42.5 |
| Comp. Ex. 5 | 52.1 | 51.0 |

As shown in Table 4 and FIG. 2, Comparative Example 4 having low formulation stability shows separation between oil phases, and thus the sun protection factors in the upper layer portion and the lower layer portion are low and are not regular. On the contrary, it can be seen that Example 3 shows a high sun protection factor like the oil-in-water type formulation of Comparative Example 5 and the same sun protection factor is retained in the upper layer portion and the lower layer portion.

This suggests that the oil-dispersed liquid type cosmetic composition according to the present disclosure realizes a high SPF value through the interfacial stabilization of oil phase ingredients and optimization of specific gravities, and thus allows for the oil phase ingredients to maintain a state dispersed uniformly in the formulation without separation.

[Test Example 3] Sensual Evaluation for Makeup Cosmetic Composition

Twenty females of 25-39 ages are allowed to apply each of the cosmetic compositions according to Example 3 and Comparative Example 5 in [Test Example 2] to their faces and to evaluate the three evaluation items of lightness, non-sticky feel and spreadability. The lightness is evaluated by determining how the cosmetic compositions are applied to a small thickness, and the non-sticky feel is evaluated by determining how the skin applied with the cosmetic compositions is not sticky. The spreadability is evaluated by determining how the cosmetic compositions are applied softly and uniformly to the skin.

The evaluation criteria for each item are based on a 5-point scale, wherein a higher point is given to a higher effect. The average points are shown in the following Table 5.

TABLE 5

| | Example 3 | Comp. Ex. 5 |
|---|---|---|
| Lightness | 5.0 | 1.2 |
| Non-sticky feel | 4.7 | 3.3 |
| Spreadability | 4.8 | 4.3 |

As can be seen from Table 5, Example 3 according to an embodiment of the present disclosure shows higher spreadability as compared to the oil-in-water type composition of Comparative Example 5, even though Example 3 is an oil-dispersed liquid type formulation. In addition, it can be seen that Example 3 has significantly improved light applicability and non-sticky fresh finishing feel upon the application to the skin as compared to the oil-in-water type composition of Comparative Example 5 having low viscosity.

[Test Example 4] Comparison of Feel of Use of Cosmetic Composition Impregnated in Foam Carrier Each of the cosmetic compositions of Example 3 and Comparative Example 5 in [Test Example 2] is supported in an ether-based polyurethane foam carrier. Each composition is taken from the foam carrier by a hand or puff and determined for the stickiness and thickness upon the application to the skin as follows.

The thickness is determined by applying 2 mg/cm$^2$ of each composition uniformly to artificial leather, drying the composition for 15 minutes and carrying out measurement by using a 3D laser microscanner (OLS-4100). The stickiness is determined by applying each composition to the backs of hands of 25-39 aged females, attaching 10 paper pieces thereto after 15 minutes and checking the number of the remaining paper pieces.

FIG. 3 shows the results of determination of thickness. The left side shows the oil-in-water type cosmetic composition of Comparative Example 5 impregnated in a foam carrier, and the right side shows the oil-dispersed liquid type cosmetic composition of Example 3 impregnated in a foam carrier. In FIG. 3, the brightness means the thickness of a formulation. The oil-in-water type cosmetic composition of Comparative Example 5 has a thickness of 123 μm, while the oil-dispersed liquid type formulation of Example 3 has a thickness of 95 μm and thus shows an actual decrease in thickness of a cosmetic film. This suggests that the composition according to the present disclosure can be applied to the skin to a smaller thickness more uniformly.

FIG. 4 shows the results of measurement of stickiness. In the case of the oil-in-water type cosmetic composition of Comparative Example 5, 6 paper pieces are attached, suggesting that it has high stickiness after application. On the contrary, in the case of Example 3 according to an embodiment of the present disclosure, since the oil evaporates after skin application and only the powder remains on the skin, no paper piece remains. Thus, Example 3 shows a non-sticky and fresh finishing feel.

[Test Example 5] Comparison of Stability of Cosmetic Composition Impregnated in Foam Carrier It can be seen from [Test Example 2] that Example 3 causes no separation for 3 days and retains its stable formulation by improving the conventional oil-dispersed liquid type formulation, which, otherwise, causes separation merely in several hours. However, as shown in FIG. 5, powder starts to be precipitated after the lapse of 3 days and a caking phenomenon occurs. After the lapse of 1 week or more, oil separation occurs slightly and inconvenience of shaking before use still remains. Thus, in this test, each of the cosmetic compositions according to Example 3 and Comparative Example 4 is supported in an ether-based polyurethane foam carrier and variations in formulation stability are observed.

FIG. 6 is a photographic view illustrating Example 3 and Comparative Example 4 supported in the foam, 3 months after they are supported. As can be seen from FIG. 6, Comparative Example 4 causes separation of the formulation with the lapse of time and shows an unstable formulation in the upper layer portion of the carrier. On the contrary, Example 3 shows a stable formulation without separation. In the case of Examples 3, the powder is prevented from precipitation and thus the formulation is not separated. This is because the oil-dispersed liquid type cosmetic composition according to the present disclosure is impregnated uniformly in the pores of the carrier and confined and retained therein. The above results suggest that since the oil-dispersed liquid type cosmetic composition is provided in a formulation impregnated in a foam carrier, the cosmetic composition according to the present disclosure can maintain its formulation stability for a long time, and thus can provide the above-mentioned improved feel of use of the composition as it is upon the skin application, while avoiding a need for shaking before use.

While the exemplary embodiments have been shown and described, it will be understood by those skilled in the art that various changes in form and details may be made thereto without departing from the scope of this disclosure as defined by the appended claims. Therefore, it is intended that the scope of the present disclosure includes all embodiments falling within the spirit and scope of the appended claims.

The invention claimed is:

1. An oil-dispersed liquid type cosmetic composition comprising:
a volatile material having a density of 0.6-0.9 g/mL;
a non-ionic silicone surfactant having a density of 0.9-1.1 g/mL and an HLB (hydrophile-lipophile balance) of 1-6;
powder; and
an organic UV protecting agent comprising at least one selected from a group consisting of octylmethoxy cinnamate, octylsalicylate, octocrylene, butylmethoxy-dibenzoylmethane, oxybenzone, octyltrizaone, menthylanthranilate, 3,4-methylbenzylidene camphor, isoamyl-p-methoxycinnamate, bisethylhexyloxyphenol methoxyphenyltriazine, and methylene bisbenzotriaz-olyltetramethylbutylphenol,
wherein the non-ionic silicone comprises PEG-10 Dimethicone.

2. The oil-dispersed liquid type cosmetic composition according to claim 1, wherein the volatile material comprises at least one material selected from the group consisting of: at least one volatile silicone oil selected from cyclomethicone, trimethicone and dimethicone having a viscosity of 2.0 centistock (cs) or lower; at least one volatile hydrocarbon oil selected from isododecane and dodecane; and ethanol.

3. The oil-dispersed liquid type cosmetic composition according to claim 1, wherein the powder comprises at least one selected from titanium dioxide, zinc oxide, silica and iron oxide.

4. The oil-dispersed liquid type cosmetic composition according to claim 1, which comprises the volatile material in an amount of 10-70 wt % based on the total weight of the composition.

5. The oil-dispersed liquid type cosmetic composition according to claim 1, which comprises the surfactant in an amount of 0.1-5 wt % based on the total weight of the composition.

6. The oil-dispersed liquid type cosmetic composition according to claim 1, which comprises the powder in an amount of 0.1-50 wt % based on the total weight of the composition.

7. The oil-dispersed liquid type cosmetic composition according to claim 1, which is for use in protecting UV rays.

8. The oil-dispersed liquid type cosmetic composition according to claim 7, which has a sun protection factor (SPF) of 30 or more and a protection grade of UVA (PA) of PA++ to PA+++.

9. A cosmetic product comprising:
the oil-dispersed liquid type cosmetic composition as defined in claim 1; and
a foam carrier in which the oil-dispersed liquid type cosmetic composition is impregnated.

10. The cosmetic product according to claim 9, wherein the foam carrier comprises polyurethane.

11. The cosmetic product according to claim 9, wherein the foam carrier comprises pores having an average size of 30-2500 μm.

12. The cosmetic product according to claim 11, wherein the oil-dispersed liquid type cosmetic composition is impregnated uniformly in the pores of the foam carrier and maintains a state distributed uniformly in the carrier.

13. The oil-dispersed liquid type cosmetic composition according to claim 1,
wherein the powder comprises inorganic UV protecting agent comprising at least one selected from titanium dioxide having an average particle size of 5-100 nm, zinc oxide having an average particle size of 5-300 nm, or iron oxide having an average particle size of 5-300 nm.

* * * * *